United States Patent [19]
Fujioka et al.

[11] Patent Number: 4,563,530
[45] Date of Patent: Jan. 7, 1986

[54] PREPARATION OF FLUOROPYRIDINES

[75] Inventors: George S. Fujioka, Walnut Creek; John C. Little, Concord, both of Calif.

[73] Assignee: The Dow Chemical Company, Midland, Mich.

[21] Appl. No.: 665,589

[22] Filed: Oct. 29, 1984

[51] Int. Cl.⁴ .................. C07D 213/26; C07D 213/57; C07D 213/61
[52] U.S. Cl. ..................................... 546/345; 546/286
[58] Field of Search ............... 546/345, 286; 570/147, 570/163, 145

[56] References Cited

U.S. PATENT DOCUMENTS 3,370,062 2/1968 Corran ................................. 546/345
4,490,534 12/1984 Fujikawa et al. ................... 546/345

Primary Examiner—Joseph Paul Brust

[57] ABSTRACT

A process for the simultaneous preparation of 2,3-difluoro- and 2,3-dichloropyridines from 3-chloro-2-fluoropyridine which comprises passing a 3-chloro-2-fluoropyridine over a carbon based catalyst, optionally in the presence of HF, at elevated temperatures, thereby forming the corresponding 2,3-dichloro- and 2,3-difluoropyridines.

8 Claims, No Drawings

PREPARATION OF FLUOROPYRIDINES

BACKGROUND OF THE INVENTION

Alkali metal fluorides are well-known agents for the conversion of ring-chlorinated pyridines to the corresponding fluoropyridines. Thus, Finger, et al. (*J. Org. Chem.* 28, 1666 1963)), found that KF in dimethyl sulfone at 200° C. over a period of time converted 2-chloropyridine to 2-fluoropyridine. Similarly, 2,3,5-trichloro- and 2,3,5,6-tetrachloropyridine gave the 2-fluoro- and 2,6-difluoro-3,5-dichloropyridines.

It is equally well-known that the exchange of chlorine on pyridine for fluorine using the nucleophilic action of fluoride ion very strongly favors replacement at the alpha- or gamma-positions of chloropyridines, with a beta-chlorine remaining essentially inert. Thus, in addition to the above cases, it has been noted by Chambers, et al. (*Proc. Chem. Soc.* 1964, 83) that pentachloropyridine, for example, strongly favors exchange at the alpha- and gamma-positions when heated to ca. 200° C. in a polar, aprotic diluent, and only under extreme conditions (anhydrous KF, 400°–500° C., 24 hr) does the exchange of the beta (3- and 5-) chlorines occur. Moreover, whenever this exchange at the beta (3 and/or 5) position has been observed, it has been limited to fully-substituted chloropyridines: the above-mentioned 2,3,5,6-tetrachloropyridine (having a hydrogen at the 4-position) gives only decomposition products under these conditions (Chambers, loc cit.). In closely-related substitution reactions, a beta-chloropyridine has been found to be 10,000–100,000 times less reactive than the alpha-chloro or gamma-chloropyridine, and theoretical explanations have been offered (Newkome and Paudler, "Contemporary Heterocyclic Chemistry", New York, John Wiley (1982), pp 262–3). European Patent Application No. 63,872 teaches that it is known to react chloropyridines with KF, in the presence or absence of a polar aprotic diluent, in order to replace chlorine by fluorine. However, EP No. 63,872 discloses on page 5 that when 2,3-dichloro-5-(trichloromethyl)-pyridine is allowed to react with KF that the chlorine in the 3-position (beta-position) remains unchanged while all the other chlorine atoms are replaced by fluorine. The resulting product is 3-chloro-2-fluoro-5-(trifluoromethyl)pyridine.

Similarly, the use of CsF as a fluorinating agent is taught in, e.g., European Patent Application Nos. 104,715 and 97,460 and in copending Application Ser. No. 564,800. These applications teach what are believed to be the first examples of direct substitution (with fluoride ion) of fluorine for the chlorine on a 3-chloropyridine having hydrogen on the ring. EP No. 97,460 cites the reaction of CsF with 3-chloro-2-cyano-5(trifluoromethyl)pyridine to yield the beta-fluoropyridine.

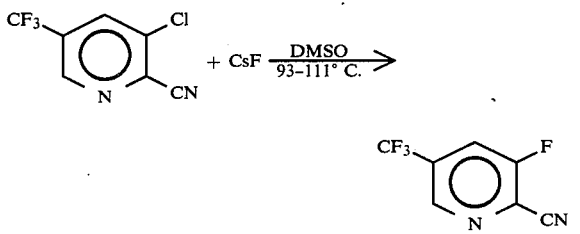

In this example, the well-known influence of an adjacent cyano group on an aromatic ring, which powerfully activates a halogen (chlorine) toward substitution (by fluoride), is believed to be operating.

EP No. 104,715 discloses that fluoride ion from cesium fluoride in an aprotic diluent will react with 3-chloro-2-fluoro-5-(trifluoromethyl)pyridine to give 2,3-difluoro-5-(trifluoromethyl)pyridine.

SUMMARY OF THE INVENTION

This invention provides a process for the simultaneous preparation of 2,3-difluoro- and 2,3-dichloropyridines from 3-chloro-2-fluoropyridines which comprises passing a compound having the formula

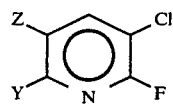

wherein Y is H, $CF_3$, Cl, F or $CH_3$ and Z is $CF_3$, Cl, F, CN, H or $CH_3$ over a carbon based catalyst, optionally in the presence of HF, at elevated temperatures, thereby forming the corresponding 2,3-dichloro- and 2,3-difluoropyridines.

The process of the present invention is illustrated by the following equation:

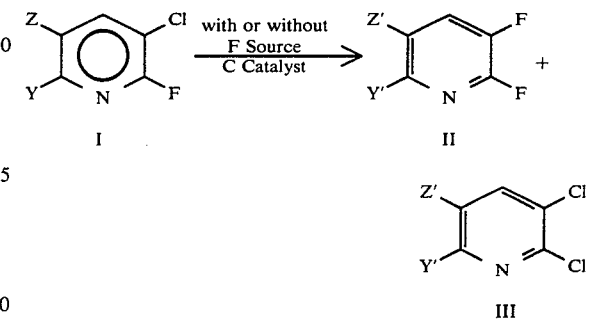

wherein Y and Z are as above defined and Y' and Z' represent Y and Z respectively and is F when either of Y and Z is F or Cl.

The 2,3-dichloro- and 2,3-difluoropyridines are intermediates useful in the preparation of herbicidal compounds as is known in the art, e.g., EP Nos. 483 and 97,460.

DETAILED DESCRIPTION OF THE INVENTION

The process of this invention is advantageously carried out at a temperature of about 350° to about 600° C., preferably at a temperature of about 400° to about 525° C. in the presence of a carbon (charcoal) based solid catalyst, preferably a high surface area, thermostable activated charcoal. Pressures of from about 0.5 to about 5 atmospheres are advantageously employed, with a pressure of about atmospheric being preferred. The contact time may vary from about 5 seconds to about 80 seconds, with a contact time of from about 10 to about 60 seconds being preferred.

In general, the products obtained from passing the 3-chloro-2-fluoropyridine (I) over the catalyst under the herein-described operating conditions include both the 2,3-difluoropyridine (II) and the 2,3-dichloropyridine, (III). The ratio of these two products can be varied by suitable choices of reaction conditions and the presence of, e.g., greater or lesser amounts of the fluorinating agent (such as HF). For example, when 3-chloro-2-fluoro-5-(trifluoromethyl)pyridine (IV) is caused to react to form V and VI in the range 400°–525° C., the higher range of temperatures and higher (greater than 1:1) mole ratios of HF:IV favor the formation of V:

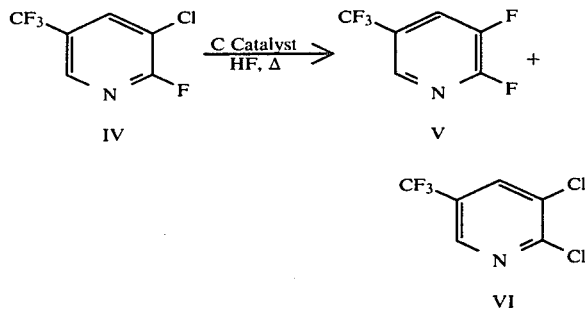

Use of higher temperatures in this system also seems to favor the formation of the products VII and VIII.

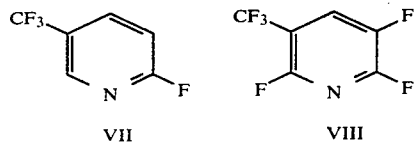

If the difluoropyridine (II) is desired as sole product, the dichloropyridine (III) may be converted back to I by treatment with fluorinating agents such as HF or KF. Compound VI, for example, yields IV in this manner:

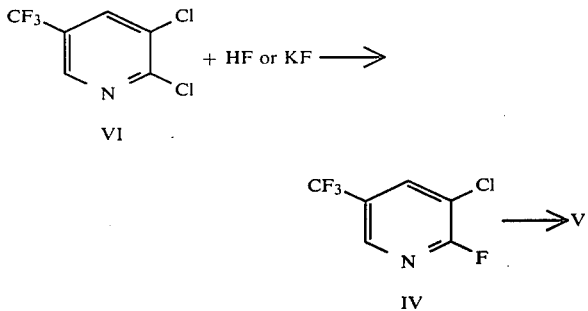

This conversion may be carried out in a separate step or, alternatively, by collecting the crude initial product, recovering the low-boiling HF and difluoride (II or IV) by distillation, and recycling the residual II (or V)+III (or VI) to the reactor with added HF.

The catalyst effective in this process may be ay commerically available activated charcoal. Conveniently used forms are granular activated charcoals such as those available from the Pittsburgh Activated Carbon Corporation, Pittsburgh, Pa., designated as PCB Carbon ®, a coconut-shell based charcoal, SGL Carbon ® and OL Carbon ®, derived from soft coals, Witco 950 ®, available from Witco Chemical Co, New York, or similar granular forms suitable for passing organic vapors through them. Alternatively, powdered forms of activated charcoal may be used in a fluidized bed reactor.

The charcoal catalyst is advantageously dried and pre-conditioned before use. For example, the granular charcoal catalysts, mentioned above, may be packed in a suitable columnar reactor and heataed while passing an inert gas such as nitrogen through the system. If anhydrous HF is to be employed, a pre-conditioning with HF at elevated temperatures is also incorporated advantageously into the process.

The invention is further illustrated by the following examples:

EXAMPLE 1

A vertically mounted ¾ inch ID by 24 inch long Hastelloy C reactor was fitted with a centrally disposed ¼ inch OD Hastelloy C thermowell and 75 grams of 8–30 mesh coconut shell-based carbon chips (PCB Carbon ®, Pittsburgh Activated Carbon Corporation, Pittsburgh, Pa.) were added. The reactor was heated to 400° C. for 2 hours using a slow (10 ml/min) stream of nitrogen to dehydrate the catalyst after which 78 grams of 3-chloro-2-fluoro-5-(trifluoromethyl)pyridine (IV) was added over 2 hours at 400° C. A receiver maintained at about 0° C. collected 41 grams of liquid which analyzed by gas-liquid phase chromatography (glpc) as 2.3% of 2,3-difluoro-5-(trifluoromethyl)pyridine (V), a 3.8% of 2,3-dichloro-5-(trifluoromethyl)pyridine (VI) and 90.1% unreacted (IV).

A purified sample of V boiled at 104°–106° C., and a purified sample of VI boiled at 169° C. The $^1$H and $^{19}$F nuclear magnetic resonance spectra were consistent with their assigned structures.

EXAMPLE 2

The reactor employed in Example 1 was charged with 76 grams of coconut shell-based carbon chips (8–30 mesh) which had been previously treated with HF and IV at 400°–425° C., and 76.5 grams of IV was added dropwise over 2.5 hours at 400°–425° C. A receiver maintained at about 0° C. collected 60 grams of product which analyzed (glpc) 7.8% V, and 5.1% of VI, the remaining being unreacted IV.

EXAMPLE 3

The reactor of Example 1 was packed with 75.5 g of 8–30 mesh coconut shell-based carbon chips, and was heated to 425° C. for 1 hour while purging with a slow stream of N$_2$ to dehydrate the system. The dried catalyst was then treated over a period of 1.5 hours at 425° C. with 7 g of anhydrous HF, and then a mixture of 77.7 g (0.39 mole) of IV and 15 g (0.75 mole) of anhydrous HF was added to the top of the reactor over a period of 5 hours at 400°–425° C. A nominal residence time of 28 sec. was calculated for the material in the catalyst zone. A total of 56 g of product was collected in a nickel receiver maintained at ca. 0° C. Analysis (glpc) of the organic portion indicated the presence of 9.6% V, 4.3% of VI and 85.6% starting material IV. Residual HF was also present. Pure V was readily recoverable by distillation, b.p. distillation, b.p. 105°–106° C. and the other products could be easily recycled to the reactor, or also recovered in pure form by distillation.

EXAMPLE 4

To the reactor described in Example 1 containing the catalyst recovered from Example 3 was added a mixture of 79.9 g (0.4 mole) of IV and 32 ml (1.6 moles) of anhydrous HF at 400°–425° C. over 5 hours. A total of 84.7 g of liquid product was collected and the organic portion was analyzed by glpc to contain ca. 11% of V, 7.1% of VI, 0.7% of 2-fluoro-5-(trifluoromethyl)-pyridine (VII) and 81.3% of unreacted starting material (IV). Residual HF was also present.

This product (84.7 g) was recycled to the top of the reactor over 2 hours at 410°–425° C. This time a total of 81.1 g of liquid product was collected with the receiver temperature being maintained near 0° C. In addition again to residual HF, the organic portion was found by glpc analysis to contain 17.4% of V, 3.9% of VI, 0.3% of VII and 77.8% of unreacted IV.

EXAMPLE 5

To the reactor described in Example 1 containing the catalyst recovered from Example 4 was charged 76.5 g (0.38 mole) of IV over 2.5 hours at 400°–425° C. No additional HF was used other than that which had been retained by the catalyst from the previous run. The product, collected as before, consisted of 60 g of material which contained some residual HF. The organic portion of glpc analysis contained 7.8% of V, 5.1% of VI, 0.3% of VII and 86.5% of unreacted IV.

EXAMPLE 6

To the reactor described in Example 1 was charged a fresh supply of 45 g of the same type of coconut shell-based catalyst as used in Example 1. The reactor was heated to 400° C. for a total of 2 hours while a slow stream of $N_2$ was used to dry the catalyst, and then 15 g of HF was added to the top of the reactor over a period of 1 hour at 400°–425° C. to pre-condition it. To the top of the reactor was added a mixture of 40 g (0.2 mole) of IV and 10 g (0.5 mole) HF over a period of 1 hour while maintaining a catalyst bed temperature of 400°–450° C. A total of 54.7 g of material was collected using a receiver temperature of 0° C. Analysis of the organic phase showed the presence of 7.1% of V, 90.3% of unreacted IV and 1.8% of VI.

The crude product (40 g) from the above experiment was diluted with 10 g of HF and again passed over the catalyst at 400°–445° C. over ca. 1¼ hours. The glpc analysis of the organic part of the 42.2 g of material recovered at ca. 0° C. showed an increase of the V to 10.3% while the VI content was raised to 4.5%; 84.5% unreacted IV was present.

EXAMPLE 7

A feedstock containing 8.7% V, 84.3% IV and 4.7% VI was split into 2 parts. To 55 g of this material was added 14 g (0.7 mole) of liquid HF (ca. 2.5:1 mole ratio of HF:pyridine) and to 56.5 g was added 20 g of liquid HF (ca. 3.5:1 HF:pyridine). Each of these mixtures was passed over the catalyst recovered from Example 6 to 400°–450° C. over ca. 1 hour. The products were collected in a receiver maintained at Dry Ice ® temperatures. For the first batch a total of 76.8 g of material was collected, analysis of the organic portion of which showed the presence of 10.6% V, 83.6% IV and 3.2% VI. Analysis by glpc of the product (58.5 g) from the second batch showed the presence of 13.1% V, 78.3% IV and 4.9% of VI.

EXAMPLE 8

To the reactor described in Example 1 was charged 48 g of 8×30 mesh soft coal-based charcoal chips (Witco 950 ®, Witco Chemical Co., New York), and the system was dried at 400°–425° C. for 2 hours with a slow stream of $N_2$. Liquid HF (20 g) was then fed to the top of the reactor at 500° C. over ca. 1¼ hours, followed by a solution of 30 g of HF and 153 g of IV over a period of 6 hours at temperatures ranging from 400° to 525° C. Samples were taken periodically and the analyses are given in Table I:

TABLE I

| Time Hrs | Avg. Col. Temp °C. | GLPC AREA % | | | | |
|---|---|---|---|---|---|---|
| | | V | IV | VI | VII | VIII |
| 1.0 | 400 | — | 95.0 | 3.5 | 0.3 | — |
| 2.0 | 425 | 4.5 | 89.3 | 4.9 | 0.7 | — |
| 3.0 | 450 | 12.0 | 72.8 | 8.7 | 3.3 | 2.8 |
| 4.0 | 475 | 14.6 | 62.9 | 8.4 | 3.7 | 7.6 |
| 5.0 | 500 | 15.6 | 70.8 | 8.1 | 0.7 | 4.7 |
| 5.5 | 525 | 20.7 | 59.1 | 8.7 | 1.0 | 9.4 |
| 6.0 | 500 | 17.4 | 69.8 | 6.2 | 1.9 | 5.3 |

EXAMPLE 9

To the reactor described in Example 1 was charged 46.3 g of the same type of coconut shell-based granular activated carbon as described in Example 1. The system was dried by heating to 500° C. with a nitrogen purge and then 153 g (0.77 mole) of IV was added over a period of 6½ hours while maintaining an average reactor temperature of 400° C. The resulting product, collected in a nickel receiver maintained at ca. 0° C., weighed 117.5 g and contained 81.0 mole % IV, 7.2% V, 11.1% VI and 0.7% VII. The calculated net yields, based on unrecovered IV were 14% V, 22% VI and 1% VII with an overall material balance of 76% based in the IV initially charged.

EXAMPLE 10

To the reactor described in Example 1 was charged 40 g of the same type of granular activated carbon as described in Example 1. The system was heated with a nitrogen purge to 500° C. for 1 hour to dry the catalyst, and then 189 g (0.94 mole) of IV containing 1.57% w/w of HF (mole ratio of HF:IV=0.16:1.00) was added over a total of 30 hours while maintaining an average reactor temperature of ca. 400° C. The resulting product, collected at ca. 0° C., weighed 634 g and showed the presence of 87.1 mole % IV, 5.0% V, 7.5% VI and 0.3% VII, in addition to some residual HF. The calculated net yields, based on unrecovered IV, were 23% V, 34% VI, and 1% VII with a calculated overall material balance of 91% based on the IV initially charged.

EXAMPLE 11

To the reactor described in Example 1 was charged 40 g of the same type of granular activated carbon as described in Example 1. The system was dried at 500° with a nitrogen purge and then a total of 276 g (1.39 moles) of IV mixed with 56 g (2.78 moles) of HF (mole ratio of HF:IV=2:1) was added over 30½ hours while maintaining an average reaction temperature of 400° C. There was collected at ca. 0° C. a total of 257 g of liquid product which was analyzed to have 72.7 mole % IV, 10.9% V, 15.6% VI and 0.8% VII. The calculated net yields, based on unrecovered IV, were 30% V, 43% VI and 2% VII with an overall material balance of 92% based on IV initially charged.

EXAMPLE 12

To the reactor described in Example 1 was charged 40 g of the same type of granular activated carbon as described in Example 1. The system was dried at 500° C. using a nitrogen purge and then a total of 173 g (0.80 moles) of 2,3-dichloro-5-(trifluoromethyl)pyridine (VI) was charged over a period of 15½ hours while maintaining an average reactor temperature of 400° C. The product collected at ca. 0° C. weighed 132 g and contained 11.7% IV, 86.7% VI, 1.7% VII and a trace of V. The net yields, based on unrecovered VI, were therefore 25% IV, 0.1% V and 3.6% VII, with an overall material balance of 75% based on VI initially charged. HF was also detected among the reaction products, presumably derived from decomposition of VI.

Various modifications may be made in the present invention without departing from the spirit or scope thereof, and it is understood that we limit ourselves only as defined in the appended claims.

EXAMPLE 13

To the reactor described in Example 1 was charged 46 g of the same type of granular activated carbon as described in Example 1. The system was dried with a nitrogen purge and heating and then a total of 244 g (1.13 moles) of 2,3-dichloro-5-(trifluoromethyl)pyridine (VI) mixed with 46 g (2.4 moles) of HF was added over 4½ hours while maintaining an average reaction temperature of 400° C. There was collected in the receiver maintained at ca. 0° C. a total of 187 g of liquid product which was neutralized over $Na_2CO_3$ and filtered to yield 174 g of oil. Analysis showed the presence of 0.3% V, 31% IV and 66% unreacted VI. Recycle of this product to the reactor leads to higher amounts of V.

We claim:
1. A process for the simultaneous preparation of 2,3-difluoro- and 2,3-dichloro-pyridines which comprises passing a compound having the formula:

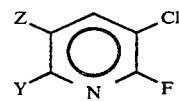

wherein Y is H, $CF_3$, Cl, F or $CH_3$ and Z is $CF_3$, Cl, F, CN, H or $CH_3$ over a thermostable, activated charcoal catalyst at a temperature of about 350° C. to about 600° C.

2. Process of claim 1 which is carried out in the presence of HF.

3. Process of claim 1 wherein the temperature is from about 400° to about 475° C.

4. Process of claim 1 wherein the pressure is from 0.5 to 5.0 atmospheres.

5. Process of claim 4 wherein the pressure is atmospheric pressure.

6. Process of claim 1 wherein the contact time is from about 5 to about 80 seconds.

7. Process of claim 6 wherein the contact time is from about 10 to about 60 seconds.

8. Process of claim 1 wherein the reactant is 3-chloro-2-fluoro-5-(trifluoromethyl)pyridine and the products are 2,3-difluoro-5-(trifluoromethyl)pyridine and 2,3-dichloro-5-(trifluoromethyl)pyridine.

* * * * *

UNITED STATES PATENT AND TRADEMARK OFFICE
CERTIFICATE OF CORRECTION

PATENT NO. : 4,563,530
DATED : January 7, 1986
INVENTOR(S) : George S. Fujioka; John C. Little It is certified that error appears in the above-identified patent and that said Letters Patent is hereby corrected as shown below:

Column 3, line 59, "ay" should read --any--; line 60, "merically" should read --mercially--.
Column 4, line 6, "heataed" should read --heated--.

Signed and Sealed this

Eighth Day of July 1986

[SEAL]

Attest:

DONALD J. QUIGG

Attesting Officer

Commissioner of Patents and Trademarks